US006508874B1

(12) United States Patent
Takai et al.

(10) Patent No.: US 6,508,874 B1
(45) Date of Patent: Jan. 21, 2003

(54) MODELING COMPOSITION, METHOD OF PREPARING MODELING MATERIAL USING SAID MODELING COMPOSITION, MODELING MATERIAL, AND MODELING METHOD USING SAID MODELING MATERIAL

(75) Inventors: Yoshikazu Takai, Fukuoka-ken (JP); Kenichi Ebata, Fukuoka-ken (JP)

(73) Assignee: Giraffe Co., Ltd., Fukuoka-ken (JP)

( * ) Notice: Subject to any disclaimer, the term of this patent is extended or adjusted under 35 U.S.C. 154(b) by 0 days.

(21) Appl. No.: 10/189,491

(22) Filed: Jul. 8, 2002

Related U.S. Application Data

(62) Division of application No. 09/529,373, filed on Apr. 12, 2000, now Pat. No. 6,432,188.

(30) Foreign Application Priority Data

Nov. 17, 1997 (JP) ............................................ 9-333509

(51) Int. Cl.[7] .................................................. C08L 5/00
(52) U.S. Cl. .............................. 106/205.31; 106/205.6; 106/205.7; 106/205.71; 106/205.9
(58) Field of Search .................. 106/205.31, 205.6, 106/205.7, 205.71, 205.9

(56) References Cited

U.S. PATENT DOCUMENTS 6,432,188 B1 * 8/2002 Takai et al. ............ 106/205.31

FOREIGN PATENT DOCUMENTS

| JP | 60-19471 A | 1/1985 |
|---|---|---|
| JP | 3-326749 A | 10/1991 |
| JP | 5-194603 A | 8/1993 |
| JP | 10-45522 A | 2/1998 |

OTHER PUBLICATIONS

JP401144947A, Nozaki et al, abstract of JP 01144947 A "Konjak' Composition and Production Thereof", Jun. 1989.

* cited by examiner

Primary Examiner—David Brunsman
(74) Attorney, Agent, or Firm—Sughrue Mion, PLLC

(57) ABSTRACT

An object of the present invention is to provide a modeling composition, which sets at room temperature by just the addition of a prescribed amount of water, is excellent in elasticity, has a high gel strength, is excellent in terms of safety, and with which a modeling material can be molded readily at low cost. The modeling composition of the present invention contains 100 weight parts of glucomannan, 1 to 100 weight parts or more preferably 2 to 75 weight parts of a basic curing agent, 9 to 500 weight parts or more preferably 50 to 250 weight parts of a neutral solute, 0 to 30 weight parts or more preferably 1 to 20 weight parts of a tempering agent, and 0 to 300 weight parts or more preferably 1 to 150 weight parts of a modifier.

52 Claims, 1 Drawing Sheet

MODELING COMPOSITION, METHOD OF PREPARING MODELING MATERIAL USING SAID MODELING COMPOSITION, MODELING MATERIAL, AND MODELING METHOD USING SAID MODELING MATERIAL

This is a divisional of application Ser. No. 09/529,373 filed Apr. 12, 2000, now U.S. Pat. No. 6,432,188 the disclosure of which is incorporated herein by reference.

TECHNICAL FIELD

The present invention concerns a modeling composition suitable for preparing modeling material for modeling rows of teeth for dental treatment or for manufacture of mouthpieces for protection of the oral cavity during rugby, boxing, or other sports activity, for modeling the external ear for the manufacture of compact, order-made hearing aids to be inserted in the external auditory canal, for modeling a foot for manufacturing order-made shoes, for modeling the digits of a hand, foot, etc., for manufacture of silicon rubber replicates, etc., for compensating for the loss of such body parts, for the manufacture of replicas of humans, animals, and other natural objects and articles, etc., for model-making and other hobbies, and for molding of automobile parts, etc. The present invention also concerns a method of preparing a modeling material using the abovementioned modeling composition, a modeling material obtained by the modeling material preparation method, and a modeling method using the abovementioned modeling material.

BACKGROUND ART

In recent years, various modeling materials have been developed, for example, for dental treatment, manufacture of protective equipment, and the modeling of parts for hobby or industrial use. For example, synthetic resins, such as polysiloxane rubbers, polysulfide rubbers, polyether rubbers, and silicone resins, and natural high polymers, such as agar and alginic acid, are used as modeling material for obtaining the impression of a row of teeth.

However, synthetic resins are cold-set by a chemical reaction, and though being easy to use, are high in cost, and in cases of use inside an oral cavity, there is a danger of clogging the bronchus since the fluidity is high. Also, when such a synthetic resin is imbibed erroneously, it may have an adverse effect on the human body since it cannot be digested. Among natural high polymer modeling materials, those having agar as the main component are thermoplastic materials. These thus accompany difficult control of temperature during handling and thus a danger of burns, etc. With modeling materials having alginic acid as the main component, large amounts of water are contained in the structural gaps of the hardened gel and since this water is released after setting, large changes occur with time and the dimensional precision is low.

Various natural high polymer modeling materials that can take the place of alginic acid and agar have thus been examined recently. Among such materials, konnyaku has been used as a food from old and since it has been confirmed to be extremely high in safety, the use of konnyaku as a modeling material is being examined.

For example, Japanese Laid-open Patent Publication No. Sho 60-19471 discloses a modeling material, which uses glucomannan and with which glucomannan and water are heated to 90° C. or more upon addition of a basic catalyst and then used for modeling, etc. However, since this modeling material requires a high temperature process, it was difficult to use on a human body.

As a glucomannan that can be set at room temperature, Japanese Laid-open Patent Publication No. Hei 5-194603 discloses a transparent glucomannan gel, which is comprised of glucomannan, a tetravalent borate, and water, and has a water content of 95 weight % to 99.5 weight %. However, since the water content is high, the gel has a low hardness even after setting and thus cannot be used as modeling material. Also, since approximately 3 hours is needed for setting, the gel was difficult to apply to the oral cavity and various other portions of the human body.

Upon careful examination towards solving the above problems, the present applicant has come to complete a cold-set modeling material comprised of glucomannan, which is set with a basic curing agent, water, a thickening agent, and a modifier, and has applied for a patent for this art by way of Japanese Patent Application No. Hei 8-227756.

However, the above prior-art modeling material that uses glucomannan was found to have the following problems.

(1) Since a basic curing agent is added afterwards, the mixing tended to be inadequate and uneven setting tended to occur.

(2) When the water content was reduced in order to make the elastic deformation factor and permanent deformation factor of the hardened gel small, the hydration of glucomannan tended to be non-uniform and the obtaining of an adequate strength became difficult.

(3) Since a basic curing agent is added to set the glucomannan, and the pH thus rises to nearly 11, there was a problem of irritation of the mucous membrane in cases of use inside an oral cavity. The excessively high pH also made use difficult as modeling material for the modeling of the digits of a hand or foot upon fracture or loss of a hand or foot, modeling for hobby goods, and other modeling purposes.

(4) Though the modeling material of alginate, etc., was kneaded upon being placed in a rubber ball in the process of modeling, the making of the gel uniform was difficult and expertise was required for the procedure. Furthermore, the prior-art modeling material had a strong adhesive force, and for example in the process of obtaining a teeth row impression, considerable labor and time were required in removing the modeling material from the teeth row of a patient and the patient was thus subjected to extreme stress and pain.

(5) Since the modeling material was too hard, patients were subjected to extreme pain in the process of modeling an external ear or ear cavity.

(6) Though plaster was normally used for the modeling of a hand or foot or the modeling of a natural object, the workability was inadequate in that the object became soiled in the process of modeling and peeling of the modeling material was difficult.

The present invention has been made to solve the above problems of the prior art and objects thereof are to provide a modeling composition, which sets at room temperature just by the addition of a prescribed amount of water, is excellent in elasticity, has a high gel strength, is excellent in terms of safety, and with which a modeling material can be formed readily at low cost, to provide a modeling material preparation method, with which a modeling material, that has a uniform surface and can accurately replicate the original, can be obtained readily, to provide a modeling material, which has plasticity in the process of modeling, loses the plasticity and changes to an elastic body in the process of removal from a subject after modeling, enables a mold that accurately maintains the three-dimensional and complex form of the original to be obtained, is low in the elastic deformation factor and permanent deformation factor after setting, enables arbitrary adjustment of the pH of the water that percolates out of the gel within a pH range of 7 to 12 without sacrificing the precision of modeling, and thus, for example, enables adjustment of the pH to 8.6 or less to lower the irritability to the oral cavity mucous membrane and provide excellent safety in the obtaining of a teeth impression and yet also enables the pH to be set higher to further increase the precision after setting in applications besides human body applications, and to provide a modeling method with which modeling can be performed by simple handling and in a short time and thus with the burden on a user or subject being alleviated.

DISCLOSURE OF THE INVENTION

In order to solve the above-described problems of the prior art, the present invention provides a modeling composition containing 100 weight parts of glucomannan, 1 to 100 weight parts or more preferably 2 to 75 weight parts of a basic curing agent, 9 to 500 weight parts or more preferably 50 to 250 weight parts of a neutral solute, 0 to 30 weight parts or more preferably 1 to 20 weight parts of a tempering agent, and 0 to 300 or more preferably 1 to 150 weight parts of a modifier.

The following excellent effects can be realized with the above arrangement.

a. A modeling material, which sets to an elastic body at room temperature simply by the addition of a prescribed amount of water, has a high gel strength, is excellent in safety, and can be molded readily at low cost, can be obtained.

b. Since prescribed amounts of basic curing agent and modifier are contained, the glucomannan content per unit amount of gel can be made higher than in the prior arts.

c. Generally, when the glucomannan content per unit amount of gel increases, the gelling rate becomes too fast, making modeling difficult and leading to significant loss in ease of handling. However, with the present invention, the setting time can be adjusted freely simply by changing the content of the neutral solute. That is, it has found that the amount of water taken in by glucomannan can be restrained by making a hydrophilic neutral solute coexist in the aqueous gelling solution. As a result, it has become possible to increase the amount of glucomannan per unit amount of gel and control the gelling rate, in other words, the rate of intake of water into glucomannan at the same time. Also, since the amount of glucomannan per unit amount of gel can be increased, the toughness of the resulting gel can be increased significantly.

d. Since modeling material can be formed simply by shaking, unlike prior arts with which the modeling material is formed by kneading the modeling composition with a spatula, the modeling material can be made extremely readily even by an unskilled person.

e. Since the modeling composition is elastic and can be peeled off readily, the workability of the modeling work can be improved considerably and the modeling yield can be improved significantly.

In the modeling material preparation method of the present invention, 100 weight parts of glucomannan, 1 to 100 weight parts or more preferably 2 to 75 weight parts of a basic curing agent, 9 to 500 weight parts or more preferably 50 to 250 weight parts of a neutral solute, 0 to 30 weight parts or more preferably 1 to 20 weight parts of a tempering agent, and 0 to 300 or more preferably 1 to 150 weight parts of a modifier are mixed with an amount of water which is 300 to 3600 weight parts or more preferably 300 to 1200 weight parts per 100 weight parts of the abovementioned glucomannan and at the same time with which the concentration of the abovementioned neutral solute will be from 3 weight % to saturated with respect to the water.

The following excellent effects can be realized by the above arrangement.

a. A modeling material, which has a uniform surface and can accurately replicate the original, can be obtained.

b. Since the modeling material has elasticity, it is excellent in peelability in the process of mold release after modeling and can be peeled off readily in a short time.

c. Since it has become possible to increase the amount of glucomannan per unit amount of gel, the toughness of the resulting gel can be increased considerably and elasticity and other forms of mechanical strength can be increased.

The modeling material of the present invention is comprised of a modeling material prepared by the above-described modeling material preparation method.

With this arrangement, modeling material, which enables high modeling precision due to the low elastic deformation factor and permanent deformation factor after setting and with which the irritability to skin, the mucous membrane inside an oral cavity, etc., can be lowered, can be obtained.

Furthermore, the modeling material of the present invention has plasticity in the process of modeling, loses the plasticity and changes to an elastic body in the process of removal from a subject after modeling, enables the obtaining of a mold that accurately maintains the three-dimensional and complex form of the original, is low in the elastic deformation factor and permanent deformation factor after setting, enables the pH of the water that percolates out of the modeling material or mold to be adjusted to a predetermined pH within a pH range of 7 to 8.6, etc., is excellent in safety, enables modeling of high precision, and can lower the irritability to skin, the mucous membrane inside an oral cavity, etc. Since the modeling material can be formed simply by shaking, the modeling material can be made extremely readily even by an unskilled person. Since the modeling material has elasticity and can be peeled off readily, the workability of the modeling work can be improved considerably and the modeling yield can be improved significantly.

The modeling method of the present invention is comprised of a pressing process in which the abovementioned modeling material is pressed against the subject to be modeled, and a setting process, in which the modeling material that has been pressed in the abovementioned pressing process is set.

By the above arrangement, since a mold can be acquired with simple handling and in a short time, the burden placed on a subject can be alleviated. Furthermore, since the modeling material has elasticity, the peelability in the process of mold release after modeling is excellent and the peeling can be performed readily in a short time.

BEST MODE FOR CARRYING OUT THE INVENTION

Figure 1A:
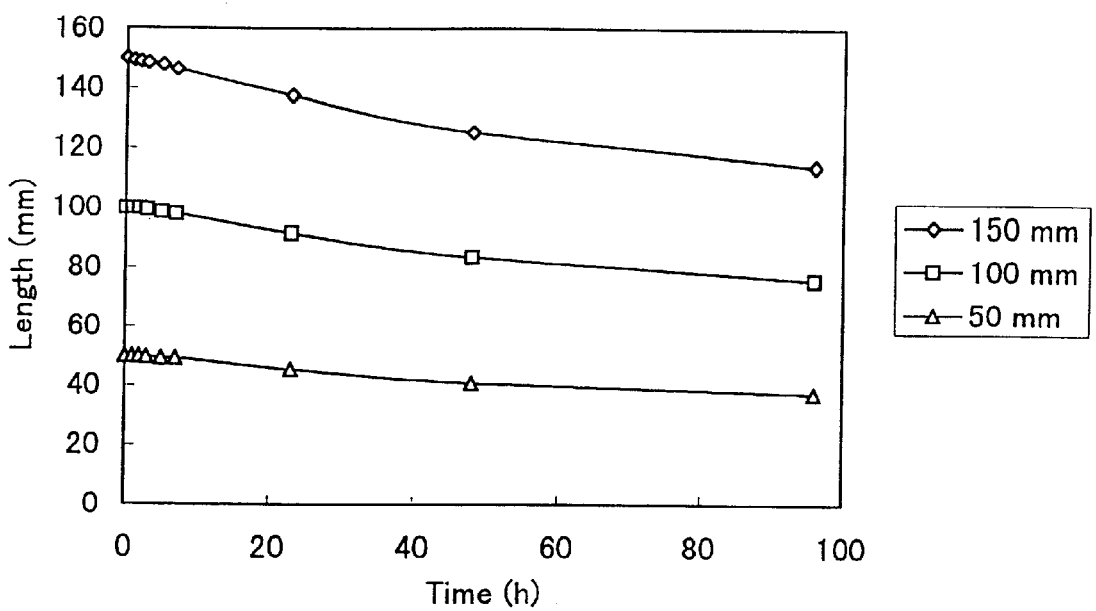
FIG. 1(*a*) shows the variation of the shrinkage factor in a water-evaporating environment and FIG. 1(*b*) shows the variation of the shrinkage factor in a non-water-evaporating environment from 5 hours after setting.

The modeling composition of the first claim of this invention contains 100 weight parts of glucomannan, 1 to 100 weight parts or more preferably 2 to 75 weight parts of a basic curing agent, 9 to 500 weight parts or more preferably 50 to 250 weight parts of a neutral solute, 0 to 30 weight parts or more preferably 1 to 20 weight parts of a tempering agent, and 0 to 300 weight parts or more preferably 1 to 150 weight parts of a modifier.

The following actions are provided by the above arrangement.

a. A modeling material can be obtained which sets to an elastic body at room temperature simply by the addition of a prescribed amount of water, has a high gel strength, is excellent in safety, and can be molded readily at low cost.

b. Since prescribed amounts of basic curing agent and modifier are contained, the glucomannan content per unit amount of gel can be made higher than in the prior arts.

c. By varying the content of the neutral solute, the rate of setting can be adjusted and a stable modeling material can be obtained simply by adding water.

Here, konnyaku mannan, comprised of grated arum root or dried arum root powder, etc., may be used favorably as the glucomannan.

The grain size of the konnyaku mannan is 30 to 250 mesh or preferably 80 to 200 mesh, and a powder with a loss upon drying of 6% or less, a protein content of 1.2% or less, a fat content of 0.2% or less, and an ash content of 1.5% or less is used favorably. This is because such a powder is excellent in dispersion properties and enables the fine shapes of an original to be reproduced accurately.

Though the results may differ according to the type of the basic curing agent, as the content of the curing agent becomes less than 2 weight parts per 100 weight parts of glucomannan, the setting rate becomes slower, causing a long time to be required for the modeling work and leading to a loss in workability as well as a tendency for the distortion factor to become large. A curing agent content that is higher than 100 weight parts is not preferable since setting tends to occur too rapidly and prior to modeling, and handling thus tends to become difficult. A basic curing agent content of less than 1 weight part or more than 100 weight parts is not preferable since the above trends become even more significant.

As the content of the neutral solute becomes less than 50 weight parts, the gelling (hydration) of glucomannan becomes inadequate and since the water content must thus be increased, the hardness after setting will tend to be low and the deformation factor will tend to be high. When the content becomes greater than 250 weight parts, the setting rate tends to become slow and a long time tends to be required for the modeling work. A content of less than 9 weight parts or more than 500 weight parts is especially unfavorable since the above trends become significant.

Though the results may differ according to the type of tempering agent, as the content of the tempering agent becomes less than 1 weight part, the gelling of glucomannan proceeds in a non-uniform manner and lumps tend to form, thus degrading the strength of the modeling material. As the content becomes greater than 20 weight parts, the physical properties of the gel (modeling material) tends to degrade somewhat and especially the deformation factor tends to degrade. A tempering agent content in excess of 30 weight parts is especially unfavorable since such trends become significant.

As the content of the modifier becomes less than 1 weight part, it becomes difficult to reproduce fine portions of the original by modeling. When the content becomes greater than 150 weight parts, aggregates (lumps) tend to form in the gel (modeling material) and, in particular, a content of more than 300 weight parts is especially unfavorable since the abovementioned trend becomes significant.

The modeling composition of the second claim of the present invention is a modeling composition of the first claim, wherein the abovementioned basic curing agent is comprised of one or more types of substances selected from among metal hydroxides, such as sodium hydroxide, potassium hydroxide, calcium hydroxide, barium hydroxide, and magnesium hydroxide, metal carbonates, such as sodium carbonate, potassium carbonate, sodium bicarbonate, potassium bicarbonate, barium carbonate, and ammonium bicarbonate, basic amino acids, such as L-arginine and L-lysine, amines, such as amyl amine, diethyl amine, and 2-amino ethanol, and borates, such as ammonium borate, calcium borate, sodium metaborate, sodium tetraborate, and methyl ammonium hydrogen tetraborate, the abovementioned neutral solute is comprised of one or more types of substances selected from among electrolytic solutes, such as sodium chloride, potassium chloride, and calcium chloride, and non-electrolytic solutes, such as glucose, sucrose, sugar, fructose, invertase, and other sugars, the abovementioned tempering agent is comprised of one or more types of substances selected from among natural high polymers such as agar, locust bean gum, tragacanth gum, carrageenan, guar gum, and pullulan, and the abovementioned modifier is comprised of one or more types of substances selected from among inorganic compounds, such as titanium oxide, activated clay, acid clay, plaster, talc, kaolin, diatomaceous earth, quartz sand, silica and other silicates, calcium carbonate, etc., and organic compounds, such as nylon powder, etc.

Here, a modifier with an average particle diameter of 0.05 to 20 $\mu$m or preferably 0.5 to 10 $\mu$m is used. The surface smoothness of the mold can thereby be improved.

This arrangement provides the following actions in addition to the actions of the first claim.

a. The elastic deformation factor, permanent deformation factor and other physical property values after setting can be controlled by selecting a suitable basic curing agent in accordance with the object on which the modeling composition is to be used. In particular, since the use of a metal hydroxide or metal carbonate will provide a high setting capability, a small amount can be used to control the physical property values and prevent the residing of undissolved matter in the gel (modeling material).

b. When a basic amino acid or amine is used, setting can be carried out under relatively mild conditions, and when a borate, etc., is used, the separation of water from the resulting gel can be restrained.

c. Since the neutral solute becomes hydrated, the rate of intake of water into the glucomannan can be lowered thereby. Since the rate of intake of water into the glucomannan can thus be controlled and the amount of glucomannan per unit amount of gel can thus be increased, the resulting gel can be significantly improved in toughness as well as made uniform and improved in surface smoothness.

d. Since a tempering agent is used, the gel can be made uniform smoothly.

e. By the tempering agent, the affinity of glucomannan with water is improved. The dispersion properties of glucomannan are therefore improved and the formation of aggregates in the gel is prevented. A uniform, paste-like modeling material can thus be obtained and the setting time can be adjusted.

f. Since the distortion factor of the glucomannan gel after setting can be lowered, the dimensional precision can be improved.

g. Since a modifier is contained, the hardness, dimensional precision, surface roughness, etc., of the glucomannan gel after setting can be improved. Thus even in cases where plaster, etc., is used to obtain a male mold from the modeling material that has set, the deformation of the set modeling material can be prevented and the surface roughness of the plaster, etc., can be improved.

In the modeling material preparation method of the third claim of the present invention, the modeling composition of either the first or second claim is mixed with an amount of water which is 300 to 3600 weight parts or more preferably 300 to 1200 weight parts per 100 weight parts of the abovementioned glucomannan and at the same time with which the concentration of the abovementioned neutral solute will be from 3 weight % to saturated with respect to the water.

The following effects are provided by this arrangement.

a. A uniform, paste-like modeling material can be obtained readily.

b. By the hydration of the neutral solute, the rate of intake of water into the glucomannan can be controlled and the surface can be made uniform.

c. Since the modeling material can be formed simply by shaking, even an unskilled person can prepare the modeling material extremely readily.

d. Since the modeling material has elasticity and can be peeled off readily, the workability of the modeling work is improved considerably, and since there is no deformation after modeling, precise replication is enabled and the yield of obtaining a successful impression can be improved significantly.

Though the results may differ according to the amounts of glucomannan and other components used, a faster setting rate and a rapid-setting modeling material can be obtained by a lower amount of water. This also provides the effect of lowering both the elastic deformation factor and the permanent deformation factor of the gel after setting.

Oppositely, when the amount of water becomes large, the setting takes place more slowly. This provides the effect of enabling work to be performed with an allowance in time even in cases where large quantities of modeling material are necessary, etc.

For example, in various industrial modeling applications, such as household electric products, automobile parts and other molded articles, food display models, etc., with which a large quantity of casting material, whether it be a plaster with a large specific gravity or a resin raw material, etc., with a relatively small specific gravity, is used in the casting process, it is favorable to set the amount of water to 300 to 600 weight parts to 100 weight parts of glucomannan so that setting will take place rapidly and the elastic deformation factor and permanent deformation factor of the gel after setting can be restrained at a low level.

In the case where a mold of the lower teeth is to be made for the manufacture of a mouthpiece, etc., the modeling frame filled with modeling material must be inverted to press the modeling material against the lower teeth, a viscosity with which the modeling material will not spill out is required, and setting must take place within a short time in order to alleviate the burden on the subject. Though the results may depend on the age of the subject, the amount of saliva secreted, etc., it was found that the amount of water should be in the range of 300 to 900 weight parts, preferably 300 to 500 weight parts, or even more preferably 300 to 400 weight parts.

In cases where the impression of another portion of the human body is to be acquired, the amount of water is preferably set in the range of 400 to 1000 weight parts, though this will depend on the portion of application, age of the subject, etc. In this case, the water temperature is preferably raised to near the body temperature in advance. Stimulation of the skin can thus be lessened and the setting rate may be increased.

In cases where the object to be modeled is small and has a relatively complex structure, such as in the making of accessories, candles, models, and other hobby applications, the amount of water is preferably set to 400 to 1200 weight parts since the modeling material will then be low in viscosity, soft, and thus excellent in workability.

The fourth claim of the present invention provides a modeling material preparation method as set forth in the third claim, wherein a. a gel forming agent, comprised of 100 weight parts of the abovementioned glucomannan, 0 to 30 weight parts or more preferably 1 to 20 weight parts of the abovementioned tempering agent, and 0 to 150 weight parts or more preferably 1 to 100 weight parts of the abovementioned modifier, and b. an aqueous solution, made by dissolving 1 to 100 weight parts or more preferably 2 to 75 weight parts of the abovementioned basic curing agent and 9 to 500 weight parts or more preferably 50 to 250 weight parts of the abovementioned neutral solute in 300 to 3600 weight parts or more preferably 300 to 1200 weight parts of water and then adding a pH adjuster to adjust the pH to 6 to 12 or more preferably 7 to 12, are prepared, and the abovementioned gel forming agent and the abovementioned aqueous solution are mixed together to prepare a modeling material.

This arrangement provides the following action in addition to the actions of the third claim.

That is, by simply mixing the abovementioned two components, a paste-like modeling material can be obtained which has plasticity in the process of modeling, loses the plasticity and changes to an elastic body in the process of removal from a subject after modeling, enables a mold that accurately maintains the three-dimensional and complex form of the original to be obtained, is low in the elastic deformation factor and permanent deformation factor after setting, enables adjustment of the pH of the water that percolates out of the gel to within a range of 7 to 8.6, etc., is excellent in safety, enables modeling of high precision, and can lower the irritability to skin, the mucous membrane inside an oral cavity, etc.

For example, in taking a teeth impression, since the pH of the modeling material can be adjusted to 8.6 or less, the irritation of the oral cavity mucous membrane can be reduced and safety can thus be increased. For human body applications besides teeth impressions, the pH can be adjusted to 9.5 or less or preferably 8.6 or less, etc.

In hobby applications where the time during which the modeling material is directly touched by hand, etc., is relatively short, the pH may be set to 10 or less.

Although the pH will normally not be a problem in industrial applications, a pH of 12 or less is preferable since safety will then be excellent, handling will be easy, etc. Adequate hardness and a low deformation factor can be achieved within this range.

Here, univalent or multivalent alcohol, such as ethyl alcohol, isopropyl alcohol, glycerin, etc., or a neutral or anionic surfactant may be added to the aqueous solution. An amount added of 1 to 10 wt % is favorable. By adding an alcohol or surfactant, the surface tension of the aqueous solution may be lowered to thereby improve the affinity of glucomannan with the aqueous solution.

The fifth claim of the present invention provides a modeling material preparation method as set forth in the fourth claim, wherein the pH adjuster is comprised of at least one type of substance selected from among organic acids, such as acetic acid, lactic acid, citric acid, tartaric acid, glycine, etc., salts of such organic acids, and inorganic acids, such as boric acid, phosphoric acid, and aluminic acid.

The above arrangement provides the following action in addition to the actions provided by the fourth claim.

That is, the pH can be adjusted readily simply by selecting the type and amount of pH adjuster, and irritation of the mucous membrane in cases where the above-described modeling material is used inside an oral cavity, etc., can thus be restrained. Here, as the pH becomes lower than 7.5, the setting rate tends to become slow. A pH higher than 8.6 is also unfavorable since the irritation of the oral cavity mucous membrane, etc., in the process of taking a teeth impression tends to become stronger and modeling processes for hobby goods and industrial parts tend to become insufficient for safety.

The sixth claim of the present invention provides a modeling material preparation method as set forth in the fourth claim, wherein the abovementioned tempering agent is comprised of 5 to 20 weight parts or more preferably 6 to 15 weight parts of agar and the abovementioned pH adjuster is comprised of 1 to 20 weight parts or more preferably 6 to 15 weight parts of acetic acid.

The above arrangement provides the following actions in addition to the actions provided by the fourth claim.

a. A uniform, paste-like modeling material can be obtained, and even in cases of use inside an oral cavity, etc., which is sensitive to stimulus, the irritation of the mucous membrane can be restrained.

b. The smoothness of the surface of hobby goods and industrial parts can be improved.

Here, if the amount of agar becomes less than 6 weight parts, the prescribed tempering effects tend to become difficult to obtain. An amount of more than 15 weight parts is also not preferable since setting tends to become slow.

The agar may be placed in the aqueous solution. The hardness after setting may thus be improved.

The seventh claim of the present invention provides a modeling material that is prepared by a modeling material preparation method of any of the third to sixth claims.

This arrangement provides an action in that since the amount of water has been decreased, the hardness after setting can be made high. Also, predetermined setting rates and physical properties after setting may be obtained by adjustment of the amount of water.

Though the results may differ according to the type and amount of neutral solute, when the amount of water becomes less than 300 weight parts, setting tends to occur too rapidly, the hydration of glucomannan tends to become non-uniform easily, and the strength after setting tends to decrease. As the amount of water becomes greater than 1200 weight parts, the setting time tends to become long, the strength tends to degrade, and the deformation factor tends to become large. In particular, an amount of water greater than 3600 weight parts is even more unfavorable as the above trends become more significant.

The modeling method of the eighth claim of the present invention is comprised of a pressing process in which the modeling material of the seventh claim is pressed against the subject to be modeled, and a setting process, in which the modeling material that has been pressed in the abovementioned pressing process is set.

The following actions are provided by this arrangement.

a. Since modeling can by performed by simple handling and in a short time, the burden placed on a subject can be alleviated, and modeling can be performed at home without requesting a doctor, etc.

b. The workability of the modeling work for hobby goods or industrial parts can be improved and modeling material of high precision can be obtained.

Embodiments of the present invention shall now be described in detail by way of examples.

First Example

As glucomannan, 10 weight parts of konnyaku mannan were used, and this was mixed uniformly with 1 weight part of agar, 15 weight parts of sugar, and 0.5 weight parts of calcium hydroxide. 0.2 weight parts of boric acid, 50 weight parts of water, and 0.65 weight parts of acetic acid were added to the above mixture. Shaking was then performed in a sealed container to obtain a uniform, paste-like modeling material.

When the modeling material thus obtained was subject to tests in accordance with 4.4 and 4.5 of JIS T-6505, the modeling material hardened gradually at room temperature and after approximately 2 minutes, the material lost plasticity and became an elastic, gel-like material.

Next, the gel-like material (modeling material) was pressed against a teeth row model and hardened. After the elapse of 3 minutes, the modeling material was removed as an impression from the teeth row model and plaster was placed and hardened in the impression to prepare a replicate a comparison showed that the impression accurately reproduced the fine shapes of the teeth row model in a detailed manner and the surface of the reproduced surface was found to have extremely good smoothness.

Upon removing the hardened modeling material from the test reproduced accurately.

After the elapse of another 10 minutes, the elastic deformation factor, the permanent deformation factor, and the pH were measured. The elastic deformation factor was 29.9% and the permanent deformation factor was 7.8%. The pH of the leachate of this model was 8.3.

In likewise manner, a teeth row model of an athlete was made and a mouthpiece was made from the model. This mouthpiece was found to decrease injuries during rugby or other rough sport activities and improve the movement ability.

Second to Sixty-Third Examples

Modeling materials were made with varying amounts of the blended components and these were tested and evaluated in accordance with 4.4 and 4.5 of JIS T-6505 as with the first example. The results are shown in Tables 1 through 7.

For evaluation of suitability according to application, the lowest evaluation point among (1) through (3) below were selected and indicated in the Tables.

(1) With regard to the elastic deformation factor $\alpha$, an $\alpha \leq 30$ was evaluated as ⊚ (excellent), an $\alpha$ such that $30 < \alpha \leq 37$ was evaluated as ○ (good), an $\alpha$ such that $37 < \alpha \leq 40$ was evaluated as $\Delta$ (satisfactory), and an $\alpha$ such that $40 < \alpha$ was evaluated as X (unsatisfactory). However in the case of hobby use, the ○ evaluation was given if the permanent deformation factor $\beta \leq 15$ even if $\alpha$ was such that $40 < \alpha$.

(2) With regard to the permanent deformation factor β, a β≦10 was evaluated as ⊚, a β such that 10<β≦15 was evaluated as ○, a β such that 15<β≦20 was evaluated as Δ, and a β such that 20<β was evaluated as X.

(3) With regard to pH, a pH<6 was evaluated as X since glucomannan does not harden readily at such a pH. Otherwise, the following standards were employed according to application.

a. Dental applications : A pH such that 6≦pH≦8.6 was evaluated as ⊚ and a pH such that 8.6<pH was evaluated as X.

b. Human body applications besides dental applications : A pH such that 6≦pH≦8.6 was evaluated as ⊚, a pH such that 8.6<pH≦9.5 was evaluated as ○, and a pH such that 9.5<pH was evaluated as X c. Hobby applications not used for the human body : A pH such that 6≦pH≦10 was evaluated as ⊚, a pH such that 10<pH≦11 was evaluated as Δ, and a pH such that 12< pH was evaluated as X.

d. Industrial use : A pH such that 6≦pH≦12 was evaluated as ⊚ and all other pH values were evaluated as X.

The results of the second to ninth examples demonstrated the following.

a. As the amount of calcium hydroxide increases, the pH increases and both the elastic deformation factor and the permanent deformation factor decrease.

b. Since it is difficult to adjust the pH to 8.6 or below when the pH is adjusted with boric acid alone, application to dental objects and other objects used inside an oral cavity and application to the external ear are difficult in this case.

c. For applications to human body parts besides dental applications as well as for hobby and industrial applications, it is preferable to increase the amount of calcium hydroxide and raise the pH as much as possible within the applicable pH range since the physical properties after hardening will then be satisfactory. This is especially suitable and highly effective for industrial applications.

The results of the tenth to seventeenth examples demonstrated the following.

When a prescribed amount of acetic acid is added, not only can the elastic deformation factor and the permanent deformation factor be held at low levels but the pH can also be held within the allowable range even when the amount of calcium hydroxide, used as the basic curing agent, is increased.

In particular, since the pH can be held at 8.6 or less while keeping the elastic deformation factor and the permanent deformation factor at low levels, this is especially favorable and useful for dental applications.

The results of the eighteenth to twenty-first examples showed that when the amount of sugar, used as the neutral solute, is increased, though the pH can be lowered somewhat, both the elastic deformation factor and permanent deformation factor increased and the increase of the permanent deformation factor was especially large.

The following were demonstrated by the twenty-second to twenty-fifth examples.

a. When the amount of agar, used as the tempering agent, was increased, both the elastic deformation factor and permanent deformation factor decreased, the tempering effect was significant, and the precision after setting could be improved.

b. Though an amount of agar of approximately 1 weight part to 100 weight parts of glucomannan (1 g to 10 g of glucomannan) is normally adequate, the surface precision improves when the amount of agar is increased further.

The results of the twenty-sixth to thirty-first examples showed that titanium oxide, while hardly affecting the elastic deformation factor and the permanent deformation factor, had a large effect in the adjustment of the color tone of the hardened gel, and it was found that it is preferable to add large amounts of titanium oxide for hobby and industrial applications. In particular, it was found that the addition of large amounts of titanium oxide is favorable in cases where a fingerprint or a scar, etc., is to be sampled and thereafter photographed, etc.

The results of the thirty-second to thirty-fifth examples demonstrated the following.

a. Sinceboric acid provides a preservative effect and can thus prevent the degradation of quality in cases where a hardened gel is to be preserved for a fixed amount of time, it is preferable to blend in a prescribed amount of boric acid.

b. As the amount of boric acid increases, though the pH decreases, since the boric acid forms an insoluble salt with calcium, the elastic deformation rate increases in particular.

The results of the thirty-sixth to forty-third examples showed that acetic acid has a large effect in lowering the pH (neutralization effect). It was also found that when acetic acid is added in excess and the pH becomes less than 6, it becomes difficult for setting to occur and the elastic deformation factor and permanent deformation rate also rise.

The results of the forty-fourth example showed that when tartaric acid is added in place of acetic acid, the pH rises somewhat. However, it was found that the use of tartaric acid is favorable for industrial applications.

The results of the forty-fifth example showed that when carrageenan is used in place of agar as the tempering agent, though the elastic deformation factor and permanent deformation factor increase somewhat, use can be made in hobby and industrial applications, and it was found that the use of carrageenan is favorable for industrial applications.

The results of the forty-sixth to forty-eighth examples showed that when kaolin, plaster, or calcium carbonate is added as the modifier in place of titanium oxide, small amounts will hardly affect the physical properties. However, it was found that titanium oxide was better for the color tone adjustment effect.

The results of the forty-ninth to fifty-second examples showed that when the amount of glucomannan was increased with the amounts of water and other blended components being fixed, the elastic deformation factor and permanent deformation factor decreased and the reproducibility of the original improved with an increasing content of glucomannan. It was also found that the modulus of elasticity and the hardness also improved.

The results of the fifty-third to fifty-sixth examples showed that with regard to the influence of the amount of water when the amounts of glucomannan and other blended components were fixed, a lower amount of water was preferable as both the elastic deformation factor and permanent deformation factor were then low. It was also found that when the amount of water is increased, the elastic deformation factor increases significantly.

The following were demonstrated by the fifty-seventh to sixty-first examples where the amount of the aqueous solution of a prescribed composition was increased while keeping the amounts of glucomannan, agar, and titanium oxide in the gel forming agent fixed.

a. With a mixing ratio of a gel forming agent to aqueous solution of 1:4, the modeling material was suitable for all applications including dental applications.

b. For industrial applications and other cases where plaster, etc., with a large specific gravity is to be cast, a usage ratio of a gel forming agent to aqueous solution of 1:6 or less is favorable and a ratio of 1:4 to 1:6 is favorable in terms of deformation factor for the taking of teeth impressions. If attention is paid to the pH, the ratio may be set to 1:8.

c. For modeling of a human body part besides the teeth, a ratio in the range 1:4 to 1:6 can be used.

d. In modeling for model making and other hobby applications where the object to be modeled is small and the shapes are complex, a ratio in the range 1:4 to 1:12, for which a leeway is provided in the setting time and the modeling material is soft and readily worked on until hardened, is favorable.

The results of the sixty-second and sixty-third examples showed that when alcohol or glycerin is added as the solvent in addition to water, since the affinity with glucomannan becomes excellent, the modeling material can be mixed uniformly rapidly.

Sixty-Fourth Example

A uniform, paste-like modeling material was obtained by adding an aqueous solution, made by dissolving 15 weight parts of sucrose, 0.5 weight parts of calcium hydroxide, 0.2 weight parts of boric acid, and 0.66 weight parts of acetic acid in 50 weight parts of water, to a mixture, made by uniformly mixing 10 weight parts of konnyaku mannan with 1 weight part of agar, and then performing shaking inside a sealed container.

The ear cavity of a subject was filled with cotton and the priority obtained modeling material was poured into a modeling frame and the ear cavity. After setting and then removing the modeling material, the modeling material was found to accurately reproduce the fine shapes in a detailed manner and the reproduced surface was found to have extremely good smoothness.

Sixty-Fifth Example

A uniform, paste-like modeling material was obtained by adding an aqueous solution, made by dissolving 9 weight parts of sodium chloride, 0.5 weight parts of calcium hydroxide, 0.2 weight parts of boric acid, and 0.5 weight parts of acetic acid in 50 weight parts of water, to a mixture, made by uniformly mixing 10 weight parts of konnyaku mannan with 1 weight part of agar, and then performing shaking inside a sealed container.

The modeling material thus obtained was poured into a modeling frame and the hand or foot of a subject was inserted into this modeling material. Upon removing the modeling material after the modeling material had set, the model material was found to accurately reproduce fingerprints and other fine shapes in a detailed manner.

Sixty-Sixth Example

A uniform, paste-like modeling material was obtained by preparing a gel forming agent by mixing 10 g of konnyaku mannan with 10 g of quartz sand, adding 40 g of aqueous solution of the same composition as that of the fifty-seventh to sixty-first examples to the gel forming agent, and performing shaking inside a sealed container. Upon transferring this modeling material into a prescribed container and leaving still, the modeling material set in 7 minutes.

The rubber hardness of the set modeling material was measured in accordance with A of 5 of JIS K6301-1995.

Although the rubber hardness immediately after curing was 0, the rubber hardness was found to increase to an adequate hardness of 70 upon drying the modeling material for 8 hours in a dryer set to 60° C. The linear shrinkage factor that accompanied the evaporation of water was 6.0%.

It was found that by shortening the drying time or lowering the drying temperature, the rubber hardness can be adjusted to 40 or less, at which mold release and holding can be carried out readily, and that the linear shrinkage factor can be lowered in the process as well.

Sixty-Seventh Example

A modeling material prepared with the same blending ratios as those of the sixtieth example was poured into three types of 2 cm ×2 cm square resin trays with lengths of 5 cm, 10 cm, and 15 cm, respectively. Measurements of the dimensional precision immediately after setting showed the setting shrinkage factor to be within ±1% in all cases and that the precision was high.

With each of the above types of model, (a) a model set still under constant-temperature, constant-humidity conditions of 21.5 to 22.0° C. air temperature and 39 to 41% humidity to cause the water to evaporate naturally and (b) a model wrapped with a wrapping sheet for 5 hours after hardening to stop the evaporation of water were prepared and the length variations of the respective models were measured. The results are shown in FIG. 1(a) and FIG. 1(b).

Figure 1B:
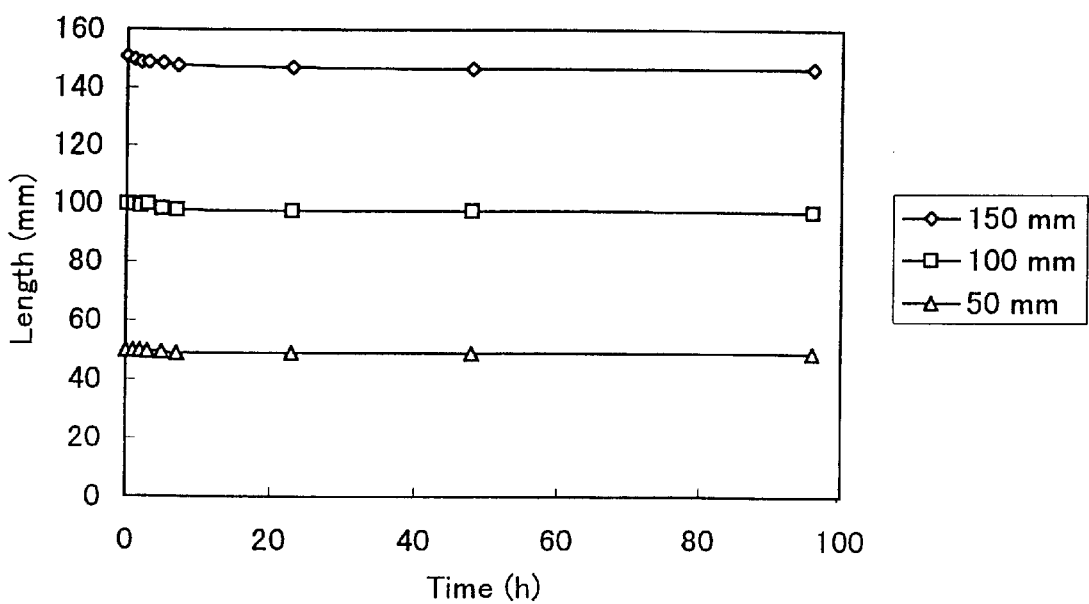

As is clear from FIG. 1(a), the modeling material was found to shrink gradually with the evaporation of water. As is clear from FIG. 1(b), it was found that the shrinkage of the modeling material could be stopped by stopping the evaporation of water in the middle.

Industrial Applicability

With the invention of the first claim of the present invention, a. Since the curing rate can be adjusted by means of the neutral solute and a stable modeling material can be obtained simply by adding a prescribed amount of water, excellent working efficiency is enabled.

In addition to the effects of the first claim, the invention of the second claim of the present invention provides the following effects.

b. Since the basic curing agent may be selected suitably in accordance with the circumstances of use, the applicable range can be expanded.

c. Since the setting ability is improved when a metal hydroxide or metal carbonate is used, the usage amount of the basic curing agent can be made small.

d. Setting can be carried out at relatively mild conditions when a basic amino acid or amine is used.

e. When a borate, etc., is used, the gel that is formed can be prevented from separating.

f. Since the affinity of glucomannan with water is improved, a uniform glucomannan gel can be obtained and the setting time can be adjusted.

g. Since the deformation factor of the glucomannan gel after setting can be lowered, the dimensional precision can be improved.

By the third claim of the present invention:

h. A uniform, paste-like modeling material can be obtained readily by simple procedures.

i. By the hydration of the neutral solute, the rate of intake of water into glucomannan can be controlled and the surface can be made uniform.

In addition to providing the effects of the invention of the third claim, the fourth claim of the present invention provides the following effects.

j. A paste-like modeling material can be obtained in the modeling process simply by mixing two components, and this modeling material has plasticity in the process of modeling, loses the plasticity and changes to an elastic body in the process of removal from a subject after modeling, and enables a mold of extremely high precision to be obtained while accurately maintaining the three-dimensionally complex form of the original.

k. The elastic deformation factor and permanent deformation factor after setting are low and the pH of the water that percolates out can be adjusted to 7 to 8.6, etc., to provide excellent safety and lower the irritation of the mucous membrane inside an oral cavity, etc., or the skin.

In addition to providing the effects of the invention of the fourth claim, the fifth claim of the present invention provides the following effects.

l. The irritation of the mucous membrane, in cases where the modeling material is to be used inside an oral cavity, etc., can be restrained.

In addition to providing the effects of the invention of the fourth claim, the sixth claim of the present invention provides the following effects.

m. Since the amount of water has been decreased, the hardness after setting can be made higher and predetermined setting rates and physical properties after setting can be obtained by adjustment of the amount of water.

By the seventh claim of the present invention:

n. The hardness, elasticity, dimensional precision, surface roughness, etc., of the glucomannan gel after setting can be improved.

o. Even in cases where plaster, etc., is used to obtain a male mold from a modeling material that has set, the deformation of the set modeling material can be prevented and the original can be reproduced accurately in the male mold of plaster, etc.

By the invention of the eighth claim of the present invention:

p. Since handling is made simple and an impression can be obtained in a short time, the burden placed on a subject can be alleviated.

q. The irritation of the mucous membrane can be restrained in cases where the modeling material is used inside an oral cavity, etc.

TABLE 1

| Types and amounts (g) of blended components | Example | | | | | | | |
|---|---|---|---|---|---|---|---|---|
| | 2 | 3 | 4 | 5 | 6 | 7 | 8 | 9 |
| Glucomannan | 10 | 10 | 10 | 10 | 10 | 10 | 10 | 10 |
| Tempering agent | | | | | | | | |
| Agar | 1 | 1 | 1 | 1 | 1 | 1 | 1 | 1 |
| Carrageenan | 0 | 0 | 0 | 0 | 0 | 0 | 0 | 0 |
| Modifier | | | | | | | | |
| Titanium oxide | 0 | 0 | 0 | 0.3 | 0.3 | 0 | 0 | 0 |
| Kaolin | 0 | 0 | 0 | 0 | 0 | 0 | 0 | 0 |
| Plaster | 0 | 0 | 0 | 0 | 0 | 0 | 0 | 0 |
| Calcium carbonate Ca | 0 | 0 | 0 | 0 | 0 | 0 | 0 | 0 |
| Basic curing agent | | | | | | | | |
| $Ca(OH)_2$ | 0.1 | 0.25 | 0.5 | 0.3 | 0.7 | 0.15 | 0.15 | 0.3 |
| NaOH | 0 | 0 | 0 | 0 | 0 | 0.11 | 0 | 0 |
| Disodium hydrogen phosphate | 0 | 0 | 0 | 0 | 0 | 0 | 0 | 0.2 |
| Neutral solute | | | | | | | | |
| NaCl | 0 | 9 | 9 | 9 | 9 | 9 | 9 | 0 |
| Sugar | 0 | 0 | 0 | 0 | 0 | 0 | 0 | 15 |
| Glucose | 0 | 0 | 0 | 0 | 0 | 0 | 9 | 0 |
| pH adjuster | | | | | | | | |
| Boric acid | 0 | 0.2 | 0.2 | 0.2 | 0.2 | 0.2 | 0.2 | 0.2 |
| Acetic acid | 0 | 0 | 0 | 0 | 0 | 0 | 0 | 0 |
| Tartaric acid | 0 | 0 | 0 | 0 | 0 | 0 | 0 | 0 |
| Solvent | | | | | | | | |
| Water | 50 | 50 | 50 | 50 | 50 | 50 | 50 | 50 |
| Alcohol | 0 | 0 | 0 | 0 | 0 | 0 | 0 | 0 |
| Glycerin | 0 | 0 | 0 | 0 | 0 | 0 | 0 | 0 |
| Measurement results | | | | | | | | |
| pH | 10.0 | 10.2 | 10.4 | 11.5 | 11.8 | 8.9 | 9.1 | 10.3 |
| Deformation factor  Elastic | 33.9 | 18.0 | 18.5 | 17.2 | 15.1 | 18.6 | 23.2 | 24.2 |
| Permanent | 11.8 | 1.9 | 3.1 | 0.9 | 0.3 | 2.1 | 4.3 | 2.3 |
| Suitability according to application | | | | | | | | |
| Dental applications | x | x | x | x | x | x | x | x |
| Human body applications | x | x | x | x | x | ○ | ◉ | x |
| Hobby applications | ○ | Δ | Δ | x | x | ◉ | ◉ | Δ |
| Industrial applications | ○ | ◉ | ◉ | ◉ | ◉ | ◉ | ◉ | ◉ |

TABLE 2

| Types and amounts (g) of blended components | Example | | | | | | | |
|---|---|---|---|---|---|---|---|---|
| | 10 | 11 | 12 | 13 | 14 | 15 | 16 | 17 |
| Glucomannan | 10 | 10 | 10 | 10 | 10 | 10 | 10 | 10 |
| Tempering agent | | | | | | | | |
| Agar | 1 | 1 | 1 | 1 | 1 | 1 | 1 | 1 |
| Carrageenan | 0 | 0 | 0 | 0 | 0 | 0 | 0 | 0 |
| Modifier | | | | | | | | |
| Titanium oxide | 0.3 | 0.3 | 0 | 0 | 0.2 | 0.3 | 0.3 | 0.3 |
| Kaolin | 0 | 0 | 0 | 0 | 0 | 0 | 0 | 0 |
| Plaster | 0 | 0 | 0 | 0 | 0 | 0 | 0 | 0 |
| Calcium carbonate Ca | 0 | 0 | 0 | 0 | 0 | 0 | 0 | 0 |
| Basic curing agent | | | | | | | | |
| $Ca(OH)_2$ | 0.1 | 0.3 | 0.5 | 0.5 | 0.5 | 0.5 | 0.7 | 0.9 |
| NaOH | 0 | 0 | 0 | 0 | 0 | 0 | 0 | 0 |
| Disodium hydrogen phosphate | 0 | 0 | 0 | 0 | 0 | 0 | 0 | 0 |
| Neutral solute | | | | | | | | |
| NaCl | 0 | 0 | 9 | 0 | 0 | 0 | 0 | 0 |
| Sugar | 15 | 15 | 0 | 15 | 15 | 15 | 15 | 15 |
| Glucose | 0 | 0 | 0 | 0 | 0 | 0 | 0 | 0 |
| pH adjuster | | | | | | | | |
| Boric acid | 0.2 | 0.2 | 0.2 | 0.2 | 0.2 | 0.2 | 0.2 | 0.2 |
| Acetic acid | 0.65 | 0.65 | 0.5 | 0.66 | 0.66 | 0.65 | 0.65 | 0.65 |
| Tartaric acid | 0 | 0 | 0 | 0 | 0 | 0 | 0 | 0 |
| Solvent | | | | | | | | |
| Water | 50 | 50 | 50 | 50 | 50 | 50 | 50 | 50 |
| Alcohol | 0 | 0 | 0 | 0 | 0 | 0 | 0 | 0 |
| Glycerin | 0 | 0 | 0 | 0 | 0 | 0 | 0 | 0 |
| Measurement results | | | | | | | | |
| pH | 4.1 | 5 | 9.6 | 8.3 | 8.3 | 8.3 | 10.9 | 11.4 |
| Deformation factor Elastic | 59.7 | 47.2 | 16.8 | 29.9 | 25.3 | 36.8 | 26.3 | 24.3 |
| Permanent | — | — | 2.8 | 7.8 | 5.4 | 9.6 | 1.4 | 1.8 |
| Suitability according to application | | | | | | | | |
| Dental applications | x | x | x | ◎ | ◎ | ○ | x | x |
| Human body applications | x | x | x | ◎ | ◎ | ○ | x | x |
| Hobby applications | x | x | ◎ | ◎ | ◎ | ○ | Δ | x |
| Industrial applications | x | x | ◎ | ◎ | ◎ | ○ | ◎ | ◎ |

TABLE 3

| Types and amounts (g) of blended components | Example | | | | | | | |
|---|---|---|---|---|---|---|---|---|
| | 18 | 19 | 20 | 21 | 22 | 23 | 24 | 25 |
| Glucomannan | 10 | 10 | 10 | 10 | 10 | 10 | 10 | 10 |
| Tempering agent | | | | | | | | |
| Agar | 1 | 1 | 1 | 1 | 0 | 0.5 | 1.5 | 2 |
| Carrageenan | 0 | 0 | 0 | 0 | 0 | 0 | 0 | 0 |
| Modifier | | | | | | | | |
| Titanium oxide | 0.3 | 0.3 | 0.3 | 0.3 | 0.3 | 0.3 | 0.3 | 0.3 |
| Kaolin | 0 | 0 | 0 | 0 | 0 | 0 | 0 | 0 |
| Plaster | 0 | 0 | 0 | 0 | 0 | 0 | 0 | 0 |
| Calcium carbonate Ca | 0 | 0 | 0 | 0 | 0 | 0 | 0 | 0 |
| Basic curing agent | | | | | | | | |
| $Ca(OH)_2$ | 0.5 | 0.5 | 0.5 | 0.5 | 0.5 | 0.5 | 0.5 | 0.5 |
| NaOH | 0 | 0 | 0 | 0 | 0 | 0 | 0 | 0 |
| Disodium hydrogen phosphate | 0 | 0 | 0 | 0 | 0 | 0 | 0 | 0 |
| Neutral solute | | | | | | | | |
| NaCl | 0 | 0 | 0 | 0 | 0 | 0 | 0 | 0 |
| Sugar | 5 | 10 | 20 | 25 | 15 | 15 | 15 | 15 |
| Glucose | 0 | 0 | 0 | 0 | 0 | 0 | 0 | 0 |

TABLE 3-continued

| Types and amounts (g) of blended components | Example | | | | | | | |
|---|---|---|---|---|---|---|---|---|
| | 18 | 19 | 20 | 21 | 22 | 23 | 24 | 25 |
| pH adjuster | | | | | | | | |
| Boric acid | 0.2 | 0.2 | 0.2 | 0.2 | 0.2 | 0.2 | 0.2 | 0.2 |
| Acetic acid | 0.65 | 0.65 | 0.65 | 0.65 | 0.65 | 0.65 | 0.65 | 0.65 |
| Tartaric acid | 0 | 0 | 0 | 0 | 0 | 0 | 0 | 0 |
| Solvent | | | | | | | | |
| Water | 50 | 50 | 50 | 50 | 50 | 50 | 50 | 50 |
| Alcohol | 0 | 0 | 0 | 0 | 0 | 0 | 0 | 0 |
| Glycerin | 0 | 0 | 0 | 0 | 0 | 0 | 0 | 0 |
| Measurement results | | | | | | | | |
| pH | 8.5 | 8.3 | 7.9 | 7.6 | 8.3 | 8.3 | 8.3 | 8.3 |
| Deformation factor   Elastic | 32.9 | 34.1 | 39.1 | 45.2 | 43.1 | 39.5 | 33.7 | 29.7 |
| Permanent | 4.1 | 6.5 | 22.8 | 34.6 | 6.9 | 8.9 | 8.5 | 5.9 |
| Suitability according to application | | | | | | | | |
| Dental applications | ○ | ○ | x | x | x | Δ | ○ | ◉ |
| Human body applications | ○ | ○ | x | x | x | Δ | ○ | ◉ |
| Hobby applications | ○ | ○ | x | x | ○ | Δ | ○ | ◉ |
| Industrial applications | ○ | ○ | x | x | x | Δ | ○ | ◉ |

TABLE 4

| Types and amounts (g) of blended components | Example | | | | | | | | | |
|---|---|---|---|---|---|---|---|---|---|---|
| | 26 | 27 | 28 | 29 | 30 | 31 | 32 | 33 | 34 | 35 |
| Glucomannan | 10 | 10 | 10 | 10 | 10 | 10 | 10 | 10 | 10 | 10 |
| Tempering agent | | | | | | | | | | |
| Agar | 1 | 1 | 1 | 1 | 1 | 1 | 1 | 1 | 1 | 1 |
| Carrageenan | 0 | 0 | 0 | 0 | 0 | 0 | 0 | 0 | 0 | 0 |
| Modifier | | | | | | | | | | |
| Titanium oxide | 0 | 0.1 | 0.5 | 0.7 | 1 | 0.3 | 0.3 | 0.3 | 0.3 | 1 |
| Kaolin | 0 | 0 | 0 | 0 | 0 | 0 | 0 | 0 | 0 | 0 |
| Plaster | 0 | 0 | 0 | 0 | 0 | 0 | 0 | 0 | 0 | 0 |
| Calcium carbonate Ca | 0 | 0 | 0 | 0 | 0 | 0 | 0 | 0 | 0 | 0 |
| Basic curing agent | | | | | | | | | | |
| $Ca(OH)_2$ | 0.5 | 0.5 | 0.5 | 0.5 | 0.5 | 0.5 | 0.5 | 0.5 | 0.5 | 0.5 |
| NaOH | 0 | 0 | 0 | 0 | 0 | 0 | 0 | 0 | 0 | 0 |
| Disodium hydrogen phosphate | 0 | 0 | 0 | 0 | 0 | 0 | 0 | 0 | 0 | 0 |
| Neutral solute | | | | | | | | | | |
| NaCl | 0 | 0 | 0 | 0 | 0 | 0 | 0 | 0 | 0 | 0 |
| Sugar | 15 | 15 | 15 | 15 | 15 | 15 | 15 | 15 | 15 | 15 |
| Glucose | 0 | 0 | 0 | 0 | 0 | 0 | 0 | 0 | 0 | 0 |
| pH adjuster | | | | | | | | | | |
| Boric acid | 0.2 | 0.2 | 0.2 | 0.2 | 0.2 | 0 | 0.1 | 0.3 | 0.4 | 0.2 |
| Acetic acid | 0.65 | 0.65 | 0.65 | 0.65 | 0 | 0.65 | 0.65 | 0.65 | 0.65 | 0.5 |
| Tartaric acid | 0 | 0 | 0 | 0 | 0 | 0 | 0 | 0 | 0 | 0 |
| Solvent | | | | | | | | | | |
| Water | 50 | 50 | 50 | 50 | 50 | 50 | 50 | 50 | 50 | 50 |
| Alcohol | 0 | 0 | 0 | 0 | 0 | 0 | 0 | 0 | 0 | 0 |
| Glycerin | 0 | 0 | 0 | 0 | 0 | 0 | 0 | 0 | 0 | 0 |
| Measurement results | | | | | | | | | | |
| pH | 8.3 | 8.3 | 8.3 | 8.3 | 11.2 | 9.5 | 10.9 | 10.1 | 7.6 | 7.4 |
| Deformation factor   Elastic | 34 | 32.4 | 34.9 | — | 23.8 | 23.5 | 26 | 34.6 | 37.3 | 36.5 |
| Permanent | 7.1 | 7.2 | 8.3 | — | 2.6 | 3.7 | 3.1 | 7 | 7 | 10.7 |
| Suitability according to application | | | | | | | | | | |
| Dental applications | ○ | ○ | ○ | x | x | x | x | x | Δ | Δ |
| Human body applications | ○ | ○ | ○ | x | x | ◉ | x | x | Δ | Δ |
| Hobby applications | ○ | ○ | ○ | x | x | ◉ | ○ | ○ | ○ | Δ |
| Industrial applications | ○ | ○ | ○ | x | ◉ | ◉ | ◉ | ○ | Δ | Δ |

TABLE 5

| Types and amounts (g) of blended components | Example | | | | | | | | |
|---|---|---|---|---|---|---|---|---|---|
| | 36 | 37 | 38 | 39 | 40 | 41 | 42 | 43 | 44 |
| Glucomannan | 10 | 10 | 10 | 10 | 10 | 10 | 10 | 10 | 10 |
| Tempering agent | | | | | | | | | |
| Agar | 1 | 1 | 1 | 1 | 1 | 1 | 1 | 1 | 1 |
| Carrageenan | 0 | 0 | 0 | 0 | 0 | 0 | 0 | 0 | 0 |
| Modifier | | | | | | | | | |
| Titanium oxide | 0.3 | 0.3 | 0 | 0 | 0.3 | 0.3 | 0.3 | 0.3 | 0 |
| Kaolin | 0 | 0 | 0 | 0 | 0 | 0 | 0 | 0 | 0 |
| Plaster | 0 | 0 | 0 | 0 | 0 | 0 | 0 | 0 | 0 |
| Calcium carbonate Ca | 0 | 0 | 0 | 0 | 0 | 0 | 0 | 0 | 0 |
| Basic curing agent | | | | | | | | | |
| $Ca(OH)_2$ | 0.5 | 0.5 | 0.5 | 0.5 | 0.5 | 0.5 | 0.5 | 0.5 | 0.3 |
| NaOH | 0 | 0 | 0 | 0 | 0 | 0 | 0 | 0 | 0 |
| Disodium hydrogen phosphate | 0 | 0 | 0 | 0 | 0 | 0 | 0 | 0 | 0 |
| Neutral solute | | | | | | | | | |
| NaCl | 0 | 0 | 0 | 0 | 0 | 9 | 9 | 9 | 15 |
| Sugar | 15 | 15 | 15 | 15 | 15 | 0 | 0 | 0 | 0 |
| Glucose | 0 | 0 | 0 | 0 | 0 | 0 | 0 | 0 | 0 |
| pH adjuster | | | | | | | | | |
| Boric acid | 0.2 | 0.2 | 0.2 | 0.2 | 0.2 | 0.2 | 0.2 | 0.2 | 0.2 |
| Acetic acid | 0.35 | 0.5 | 0.66 | 0.7 | 0.8 | 0.5 | 0.65 | 0.8 | 0 |
| Tartaric acid | 0 | 0 | 0 | 0 | 0 | 0 | 0 | 0 | 1 |
| Solvent | | | | | | | | | |
| Water | 50 | 50 | 50 | 50 | 50 | 50 | 50 | 50 | 50 |
| Alcohol | 0 | 0 | 0 | 0 | 0 | 0 | 0 | 0 | 0 |
| Glycerin | 0 | 0 | 0 | 0 | 0 | 0 | 0 | 0 | 0 |
| Measurement results | | | | | | | | | |
| pH | 11 | 8.9 | 8.5 | 8.2 | 5.9 | 10.5 | 9 | 6.2 | 10.9 |
| Deformation factor Elastic | 22.4 | 26.2 | 34.7 | 42.5 | — | 17.7 | 21.6 | 28.2 | 27.3 |
| Permanent | 0.7 | 2.3 | 11.1 | 17.3 | — | 1 | 3.6 | 5.6 | 5.3 |
| Suitability according to application | | | | | | | | | |
| Dental applications | x | x | ○ | x | x | x | x | ○ | x |
| Human body applications | x | ◎ | ○ | x | x | x | ◎ | ◎ | x |
| Hobby applications | Δ | ◎ | ○ | x | x | Δ | ◎ | ◎ | Δ |
| Industrial applications | ◎ | ◎ | ○ | x | x | ◎ | ◎ | ◎ | ◎ |

TABLE 6

| Types and amounts (g) of blended components | Example | | | | | | | |
|---|---|---|---|---|---|---|---|---|
| | 45 | 46 | 47 | 48 | 49 | 50 | 51 | 52 |
| Glucomannan | 10 | 10 | 10 | 10 | 10 | 11 | 12 | 15 |
| Tempering agent | | | | | | | | |
| Agar | 0 | 1 | 1 | 1 | 1 | 1 | 1 | 1 |
| Carrageenan | 1 | 0 | 0 | 0 | 0 | 0 | 0 | 0 |
| Modifier | | | | | | | | |
| Titanium oxide | 0 | 0 | 0 | 0 | 0 | 0 | 0 | 0 |
| Kaolin | 0 | 5 | 0 | 0 | 0 | 0 | 0 | 0 |
| Plaster | 0 | 0 | 1 | 0 | 0 | 0 | 0 | 0 |
| Calcium carbonate Ca | 0 | 0 | 0 | 1 | 0 | 0 | 0 | 0 |
| Basic curing agent | | | | | | | | |
| $Ca(OH)_2$ | 0.3 | 0.3 | 0.3 | 0.3 | 0.5 | 0.5 | 0.5 | 0.5 |
| NaOH | 0 | 0 | 0 | 0 | 0 | 0 | 0 | 0 |
| Sodium hydrogen phosphate | 0 | 0 | 0 | 0 | 0 | 0 | 0 | 0 |
| Neutral solute | | | | | | | | |
| NaCl | 0 | 0 | 0 | 0 | 0 | 0 | 0 | 0 |
| Sugar | 15 | 15 | 15 | 15 | 15 | 15 | 15 | 15 |
| Glucose | 0 | 0 | 0 | 0 | 0 | 0 | 0 | 0 |

TABLE 6-continued

| Types and amounts (g) of blended components | Example | | | | | | | |
|---|---|---|---|---|---|---|---|---|
| | 45 | 46 | 47 | 48 | 49 | 50 | 51 | 52 |
| pH adjuster | | | | | | | | |
| Boric acid | 0.2 | 0.2 | 0.2 | 0.2 | 0.2 | 0.2 | 0.2 | 0.2 |
| Acetic acid | 0 | 0 | 0 | 0 | 0.66 | 0.66 | 0.66 | 0.66 |
| Tartaric acid | 0 | 0 | 0 | 0 | 0 | 0 | 0 | 0 |
| Solvent | | | | | | | | |
| Water | 50 | 50 | 50 | 50 | 50 | 50 | 50 | 50 |
| Alcohol | 0 | 0 | 0 | 0 | 0 | 0 | 0 | 0 |
| Glycerin | 0 | 0 | 0 | 0 | 0 | 0 | 0 | 0 |
| Measurement results | | | | | | | | |
| pH | 10.9 | 10.5 | 10.5 | 8.3 | 8.3 | 8.3 | 8.3 | 8.3 |
| Deformation factor   Elastic | 27.8 | 27.8 | 22 | 21 | 29.9 | 27.5 | 27 | 22.2 |
| Permanent | 4.1 | 4.1 | 3.4 | 2.9 | 7.8 | 6.2 | 5.5 | 4.9 |
| Suitability according to application | | | | | | | | |
| Dental applications | x | x | x | x | ◉ | ◉ | ◉ | ◉ |
| Human body applications | x | x | x | x | ◉ | ◉ | ◉ | ◉ |
| Hobby applications | Δ | Δ | Δ | Δ | ◉ | ◉ | ◉ | ◉ |
| Industrial applications | ◉ | ◉ | ◉ | ◉ | ◉ | ◉ | ◉ | ◉ |

TABLE 7

| Types and amounts (g) of blended components | Example | | | | | | |
|---|---|---|---|---|---|---|---|
| | 57 | 58 | 59 | 60 | 61 | 62 | 63 |
| Glucomannan | 10 | 10 | 10 | 10 | 10 | 10 | 10 |
| Tempering agent | | | | | | | |
| Agar | 1 | 1 | 1 | 1 | 1 | 1 | 1 |
| Carrageenan | 0 | 0 | 0 | 0 | 0 | 0 | 0 |
| Modifier | | | | | | | |
| Titanium oxide | 0.3 | 0.3 | 0.3 | 0.3 | 0.3 | 0 | 0 |
| Kaolin | 0 | 0 | 0 | 0 | 0 | 0 | 0 |
| Plaster | 0 | 0 | 0 | 0 | 0 | 0 | 0 |
| Calcium carbonate Ca | 0 | 0 | 0 | 0 | 0 | 0 | 0 |
| Basic curing agent | | | | | | | |
| Ca(OH)$_2$ | Composition of aqueous solution | | | | | 0.5 | 0.3 |
| NaOH | (weight ratio) | | | | | 0 | 0 |
| Sodium hydrogen phosphate | Ca(OH)$_2$:Sugar:Boric acid:Acetic | | | | | 0 | 0 |
| Neutral solute | acid:Water = 0.5:15:0.2:0.65:50 | | | | | | |
| NaCl | | | | | | 9 | 0 |
| Sugar | | | | | | 0 | 15 |
| Glucose | | | | | | 0 | 0 |
| pH adjuster | | | | | | | |
| Boric acid | | | | | | 0.2 | 0.2 |
| Acetic acid | | | | | | 0 | 0 |
| Tartaric acid | | | | | | 0 | 0 |
| Solvent | | | | | | | |
| Water | | | | | | 45 | 50 |
| Alcohol | | | | | | 5 | 0 |
| Glycerin | | | | | | 0 | 1 |
| Mixing ratio (Gel forming agent:Aqueous solution) | 1:4 | 1:6 | 1:8 | 1:10 | 1:12 | | |
| Measurement results | | | | | | | |
| pH | 8.3 | 8.3 | 8.3 | 8.3 | 8.3 | 10.4 | 11.2 |
| Deformation factor   Elastic | 25.6 | 36.8 | 43 | 46.8 | 48.2 | 15.9 | 26.7 |
| Permanent | 5.2 | 7.8 | 9.8 | 14.3 | 20.4 | 1.5 | 3.7 |
| Suitability according to application | | | | | | | |
| Dental applications | ◉ | ○ | x | x | x | x | x |
| Human body applications | ◉ | ○ | x | x | x | x | x |

TABLE 7-continued

| Types and amounts (g) of blended components | Example | | | | | | |
|---|---|---|---|---|---|---|---|
| | 57 | 58 | 59 | 60 | 61 | 62 | 63 |
| Hobby applications | ⊚ | ○ | ○ | ○ | x | △ | x |
| Industrial applications | ⊚ | ○ | x | x | x | ⊚ | ⊚ |

What is claimed is:

1. A modeling material characterized in being prepared by a modeling material preparation method wherein
   (a) a gel forming agent, comprised of 100 weight parts of konnyaku mannan, 1 to 30 weight parts of tempering agent, and 1 to 150 weight parts of modifier, and
   (b) an aqueous solution, made by dissolving 1 to 100 weight parts of basic curing agent and 9 to 500 weight parts of neutral solute in 300 to 3600 weight parts of water and then adding a pH adjuster to adjust the pH to 6 to 12, are prepared, and said gel forming agent and said aqueous solution are mixed together prior to preparation of a modeling material.

2. A modeling method comprised of a pressing process in which the modeling material of claim 1 is pressed against the subject to be modeled, and a setting process, in which said modeling material that has been pressed in said pressing process is set.

3. A modeling material as set forth in claim 1, wherein said tempering agent is comprised of 5 to 20 weight parts of agar and said pH adjuster is comprised of 1 to 20 weight parts of acetic acid.

4. A modeling method comprised of a pressing process in which the modeling material of claim 3 is pressed against the subject to be modeled, and a setting process, in which said modeling material that has been pressed in said pressing process is set.

5. A modeling material as set forth in claim 3, wherein said agar is 6 to 15 weight parts and said acetic acid is 6 to 15 weight parts.

6. A modeling method comprised of a pressing process in which the modeling material of claim 5 is pressed against the subject to be modeled, and a setting process, in which said modeling material that has been pressed in said pressing process is set.

7. A modeling material as set forth in claim 1, wherein said basic curing agent is comprised of one or more substances selected from among a metal hydroxide, a metal carbonate, a basic amino acid, an amine, and a borate,
   said neutral solute is comprised of one or more substances selected from an electrolytic solute and a non-electrolytic solute,
   said tempering agent is comprised of one or more substances selected from a natural high polymer, and
   said modifier is comprised of one or more substances selected from an inorganic compound and an organic compound.

8. A modeling method comprised of a pressing process in which the modeling material of claim 7 is pressed against the subject to be modeled, and a setting process, in which said modeling material that has been pressed in said pressing process is set.

9. A modeling material as set forth in claim 7, wherein said metal hydroxide is comprised of sodium hydroxide, potassium hydroxide, calcium hydroxide, barium hydroxide, and magnesium hydroxide,
   said metal carbonate is comprised of sodium carbonate, potassium carbonate, sodium bicarbonate, potassium bicarbonate, barium carbonate, and ammonium bicarbonate,
   said basic amino acid is comprised of L-arginine and L-lysine, said amine is comprised of amyl amine, diethyl amine, and 2-amino ethanol,
   said borate is comprised of ammonium borate, calcium borate, sodium metaborate, sodium tetraborate, and methyl ammonium hydrogen tetraborate,
   said electrolytic solute is comprised of sodium chloride, potassium chloride, and calcium chloride,
   said non-electrolytic solute is comprised of saccharide,
   said natural high polymer is comprised of agar, locust bean gum, tragacanth gum, carrageenan, guar gum, and pullulan,
   said inorganic compound is comprised of silicate, titanium oxide, plaster, and calcium carbonate, and
   said organic compound is comprised of nylon powder.

10. A modeling method comprised of a pressing process in which the modeling material of claim 9 is pressed against the subject to be modeled, and a setting process, in which said modeling material that has been pressed in said pressing process is set.

11. A modeling material as set forth in claim 9, wherein said saccharide is comprised of glucose, sucrose, fructose and invert sugar, and said silicate is comprised of activated clay, acid clay, talc, kaolin, diatomaceous earth, quartz sand, and silica.

12. A modeling method comprised of a pressing process in which the modeling material of claim 11 is pressed against the subject to be modeled, and a setting process, in which said modeling material that has been pressed in said pressing process is set.

13. A modeling material as set forth in claim 1, wherein said tempering agent is 1 to 20 weight parts, said modifier is 1 to 100 weight parts, said basic curing agent is 2 to 75 weight parts, said neutral solute is 50 to 250 weight parts, said water is 300 to 1200 weight parts and said pH is 7 to 12.

14. A modeling method comprised of a pressing process in which the modeling material of claim 13 is pressed against the subject to be modeled, and a setting process, in which said modeling material that has been pressed in said pressing process is set.

15. A modeling material as set forth in claim 13, wherein said basic curing agent is comprised of one or more substances selected from among a metal hydroxide, a metal carbonate, a basic amino acid, an amine, and a borate,
   said neutral solute is comprised of one or more substances selected from an electrolytic solute and a non-electrolytic solute,
   said tempering agent is comprised of one or more substances selected from a natural high polymer, and
   said modifier is comprised of one or more substances selected from an inorganic compound and an organic compound.

16. A modeling method comprised of a pressing process in which the modeling material of claim 15 is pressed against the subject to be modeled, and a setting process, in which said modeling material that has been pressed in said pressing process is set.

17. A modeling material as set forth in claim 15, wherein said metal hydroxide is comprised of sodium hydroxide, potassium hydroxide, calcium hydroxide, barium hydroxide, and magnesium hydroxide, said metal carbonate is comprised of sodium carbonate, potassium carbonate, sodium bicarbonate, potassium bicarbonate, barium carbonate, and ammonium bicarbonate, said basic amino acid is comprised of L-arginine and L-lysine, said amine is comprised of amyl amine, diethyl amine, and 2-amino ethanol, said borate is comprised of ammonium borate, calcium borate, sodium metaborate, sodium tetraborate, and methyl ammonium hydrogen tetraborate, said electrolytic solute is comprised of sodium chloride, potassium chloride, and calcium chloride, said non-electrolytic solute is comprised of saccharide, said natural high polymer is comprised of agar, locust bean gum, tragacanth gum, carrageenan, guar gum, and pullulan, said inorganic compound is comprised of silicate, titanium oxide, plaster, and calcium carbonate, and said organic compound is comprised of nylon powder.

18. A modeling method comprised of a pressing process in which the modeling material of claim 17 is pressed against the subject to be modeled, and a setting process, in which said modeling material that has been pressed in said pressing process is set.

19. A modeling material as set forth in claim 17, wherein said saccharide is comprised of glucose, sucrose, fructose and invert sugar, and said silicate is comprised of activated clay, acid clay, talc, kaolin, diatomaceous earth, quartz sand, and silica.

20. A modeling method comprised of a pressing process in which the modeling material of claim 19 is pressed against the subject to be modeled, and a setting process, in which said modeling material that has been pressed in said pressing process is set.

21. A modeling material as set forth in claim 1, wherein said pH adjuster is comprised of at least one substance selected from among an organic acid, a salt of such an organic acid, and an inorganic acid.

22. A modeling method comprised of a pressing process in which the modeling material of claim 21 is pressed against the subject to be modeled, and a setting process, in which said modeling material that has been pressed in said pressing process is set.

23. A modeling material as set forth in claim 21, wherein said basic curing agent is comprised of one or more substances selected from among a metal hydroxide, a metal carbonate, a basic amino acid, an amine, and a borate, said neutral solute is comprised of one or more substances selected from an electrolytic solute and a non-electrolytic solute, said tempering agent is comprised of one or more substances selected from a natural high polymer, and said modifier is comprised of one or more substances selected from an inorganic compound and an organic compound.

24. A modeling method comprised of a pressing process in which the modeling material of claim 21 is pressed against the subject to be modeled, and a setting process, in which said modeling material that has been pressed in said pressing process is set.

25. A modeling material as set forth in claim 23, wherein said metal hydroxide is comprised of sodium hydroxide, potassium hydroxide, calcium hydroxide, barium hydroxide, and magnesium hydroxide, said metal carbonate is comprised of sodium carbonate, potassium carbonate, sodium bicarbonate, potassium bicarbonate, barium carbonate, and ammonium bicarbonate, said basic amino acid is comprised of L-arginine and L-lysine, said amine is comprised of amyl amine, diethyl amine, and 2-amino ethanol, said borate is comprised of ammonium borate, calcium borate, sodium metaborate, sodium tetraborate, and methyl ammonium hydrogen tetraborate, said electrolytic solute is comprised of sodium chloride, potassium chloride, and calcium chloride, said non-electrolytic solute is comprised of saccharide, said natural high polymer is comprised of agar, locust bean gum, tragacanth gum, carrageenan, guar gum, and pullulan, said inorganic compound is comprised of silicate, titanium oxide, plaster, and calcium carbonate, and said organic compound is comprised of nylon powder.

26. A modeling method comprised of a pressing process in which the modeling material of claim 25 is pressed against the subject to be modeled, and a setting process, in which said modeling material that has been pressed in said pressing process is set.

27. A modeling material as set forth in claim 25, wherein said saccharide is comprised of glucose, sucrose, fructose and invert sugar, and said silicate is comprised of activated clay, acid clay, talc, kaolin, diatomaceous earth, quartz sand, and silica.

28. A modeling method comprised of a pressing process in which the modeling material of claim 27 is pressed against the subject to be modeled, and a setting process, in which said modeling material that has been pressed in said pressing process is set.

29. A modeling material as set forth in claim 21, wherein said tempering agent is 1 to 20 weight parts, said modifier is 1 to 100 weight parts, said basic curing agent is 2 to 75 weight parts, said neutral solute is 50 to 250 weight parts, said water is 300 to 1200 weight parts and said pH is 7 to 12.

30. A modeling method comprised of a pressing process in which the modeling material of claim 29 is pressed against the subject to be modeled, and a setting process, in which said modeling material that has been pressed in said pressing process is set.

31. A modeling material as set forth in claim 29, wherein said basic curing agent is comprised of one or more substances selected from among a metal hydroxide, a metal carbonate, a basic amino acid, an amine, and a borate, said neutral solute is comprised of one or more substances selected from an electrolytic solute and a non-electrolytic solute, said tempering agent is comprised of one or more substances selected from a natural high polymer, and said modifier is comprised of one or more substances selected from an inorganic compound and an organic compound.

32. A modeling method comprised of a pressing process in which the modeling material of claim 31 is pressed against the subject to be modeled, and a setting process, in which said modeling material that has been pressed in said pressing process is set.

33. A modeling material as set forth in claim 31, wherein said metal hydroxide is comprised of sodium hydroxide, potassium hydroxide, calcium hydroxide, barium hydroxide, and magnesium hydroxide, said metal carbonate is comprised of sodium carbonate, potassium carbonate, sodium bicarbonate, potassium bicarbonate, barium carbonate, and ammonium bicarbonate, said basic amino acid is comprised of L-arginine and L-lysine, said amine is comprised of amyl amine, diethyl amine, and 2-amino ethanol, said borate is comprised of ammonium borate, calcium borate, sodium metaborate, sodium tetraborate, and methyl ammonium hydrogen tetraborate, said electrolytic solute is comprised of sodium chloride, potassium chloride, and calcium chloride, said non-electrolytic solute is comprised of saccharide, said natural high polymer is comprised of agar, locust bean gum, tragacanth gum, carrageenan, guar gum, and pullulan, said inorganic compound is comprised of silicate, titanium oxide, plaster, and calcium carbonate, and said organic compound is comprised of nylon powder.

34. A modeling method comprised of a pressing process in which the modeling material of claim 33 is pressed against the subject to be modeled, and a setting process, in which said modeling material that has been pressed in said pressing process is set.

35. A modeling material as set forth in claim 33, wherein said saccharide is comprised of glucose, sucrose, fructose and invert sugar, and said silicate is comprised of activated clay, acid clay, talc, kaolin, diatomaceous earth, quartz sand, and silica.

36. A modeling method comprised of a pressing process in which the modeling material of claim 35 is pressed against the subject to be modeled, and a setting process, in which said modeling material that has been pressed in said pressing process is set.

37. A modeling material as set forth in claim 21, wherein said organic acid is comprised of acetic acid, lactic acid, citric acid, tartaric acid, and glycine, and said inorganic acid is comprised of boric acid, phosphoric acid, and aluminic acid.

38. A modeling method comprised of a pressing process in which the modeling material of claim 37 is pressed against the subject to be modeled, and a setting process, in which said modeling material that has been pressed in said pressing process is set.

39. A modeling material as set forth in claim 37, wherein said basic curing agent is comprised of one or more substances selected from among a metal hydroxide, a metal carbonate, a basic amino acid, an amine, and a borate, said neutral solute is comprised of one or more substances selected from an electrolytic solute and a non-electrolytic solute, said tempering agent is comprised of one or more substances selected from a natural high polymer, and said modifier is comprised of one or more substances selected from an inorganic compound and an organic compound.

40. A modeling method comprised of a pressing process in which the modeling material of claim 39 is pressed against the subject to be modeled, and a setting process, in which said modeling material that has been pressed in said pressing process is set.

41. A modeling material as set forth in claim 39, wherein said metal hydroxide is comprised of sodium hydroxide, potassium hydroxide, calcium hydroxide, barium hydroxide, and magnesium hydroxide, said metal carbonate is comprised of sodium carbonate, potassium carbonate, sodium bicarbonate, potassium bicarbonate, barium carbonate, and ammonium bicarbonate, said basic amino acid is comprised of L-arginine and L-lysine, said amine is comprised of amyl amine, diethyl amine, and 2-amino ethanol, said borate is comprised of ammonium borate, calcium borate, sodium metaborate, sodium tetraborate, and methyl ammonium hydrogen tetraborate, said electrolytic solute is comprised of sodium chloride, potassium chloride, and calcium chloride, said non-electrolytic solute is comprised of saccharide, said natural high polymer is comprised of agar, locust bean gum, tragacanth gum, carrageenan, guar gum, and pullulan, said inorganic compound is comprised of silicate, titanium oxide, plaster, and calcium carbonate, and said organic compound is comprised of nylon powder.

42. A modeling method comprised of a pressing process in which the modeling material of claim 41 is pressed against the subject to be modeled, and a setting process, in which said modeling material that has been pressed in said pressing process is set.

43. A modeling material as set forth in claim 41, wherein said saccharide is comprised of glucose, sucrose, fructose and invert sugar, and said silicate is comprised of activated clay, acid clay, talc, kaolin, diatomaceous earth, quartz sand, and silica.

44. A modeling method comprised of a pressing process in which the modeling material of claim 43 is pressed against the subject to be modeled, and a setting process, in which said modeling material that has been pressed in said pressing process is set.

45. A modeling material as set forth in claim 37, wherein said tempering agent is 1 to 20 weight parts, said modifier is 1 to 100 weight parts, said basic curing agent is 2 to 75 weight parts, said neutral solute is 50 to 250 weight parts, said water is 300 to 1200 weight parts and said pH is 7 to 12.

46. A modeling method comprised of a pressing process in which the modeling material of claim 45 is pressed against the subject to be modeled, and a setting process, in which said modeling material that has been pressed in said pressing process is set.

47. A modeling material as set forth in claim 45, wherein said basic curing agent is comprised of one or more substances selected from among a metal hydroxide, a metal carbonate, a basic amino acid, an amine, and a borate, said neutral solute is comprised of one or more substances selected from an electrolytic solute and a non-electrolytic solute, said tempering agent is comprised of one or more substances selected from a natural high polymer, and said modifier is comprised of one or more substances selected from an inorganic compound and an organic compound.

48. A modeling method comprised of a pressing process in which the modeling material of claim 47 is pressed against the subject to be modeled, and a setting process, in which said modeling material that has been pressed in said pressing process is set.

49. A modeling material as set forth in claim 47, wherein said metal hydroxide is comprised of sodium hydroxide, potassium hydroxide, calcium hydroxide, barium hydroxide, and magnesium hydroxide, said metal carbonate is comprised of sodium carbonate, potassium carbonate, sodium bicarbonate, potassium bicarbonate, barium carbonate, and ammonium bicarbonate, said basic amino acid is comprised of L-arginine and L-lysine, said amine is comprised of amyl amine, diethyl amine, and 2-amino ethanol, said borate is comprised of ammonium borate, calcium borate, sodium metaborate, sodium tetraborate, and methyl ammonium hydrogen tetraborate, said electrolytic solute is comprised of sodium chloride, potassium chloride, and calcium chloride, said non-electrolytic solute is comprised of saccharide, said natural high polymer is comprised of agar, locust bean gum, tragacanth gum, carrageenan, guar gum, and pullulan, said inorganic compound is comprised of silicate, titanium oxide, plaster, and calcium carbonate, and said organic compound is comprised of nylon powder.

50. A modeling method comprised of a pressing process in which the modeling material of claim 49 is pressed against the subject to be modeled, and a setting process, in which said modeling material that has been pressed in said pressing process is set.

51. A modeling material as set forth in claim 49, wherein said saccharide is comprised of glucose, sucrose, fructose and invert sugar, and said silicate is comprised of activated clay, acid clay, talc, kaolin, diatomaceous earth, quartz sand, and silica.

52. A modeling method comprised of a pressing process in which the modeling material of claim 51 is pressed against the subject to be modeled, and a setting process, in which said modeling material that has been pressed in said pressing process is set.

\* \* \* \* \*